United States Patent [19]

Knifton et al.

[11] 3,996,293

[45] * Dec. 7, 1976

[54] SELECTIVE HYDROFORMYLATION PROCESS

[75] Inventors: John F. Knifton, Poughquag, N.Y.; Irving Schwager, Lompoc, Calif.

[73] Assignee: Texaco Inc., New York, N.Y.

[ * ] Notice: The portion of the term of this patent subsequent to Sept. 21, 1993, has been disclaimed.

[22] Filed: Oct. 3, 1973

[21] Appl. No.: 402,935

Related U.S. Application Data

[63] Continuation-in-part of Ser. No. 251,639, May 8, 1972.

[52] U.S. Cl. .......................................... 260/604 HF
[51] Int. Cl.² .......................................... C07C 45/08
[58] Field of Search ............................... 260/604 HF

[56] References Cited

FOREIGN PATENTS OR APPLICATIONS

1,138,601   1/1969   United Kingdom ......... 260/604 HF

OTHER PUBLICATIONS

Bailar et al., JACS, vol. 89, pp. 1592–1599, 1967.

*Primary Examiner*—James O. Thomas, Jr.
*Assistant Examiner*—W. B. Lone
*Attorney, Agent, or Firm*—T. H. Whaley; C. G. Ries; Bernard Marlowe

[57] ABSTRACT

This invention relates to a process for preferentially and selectively hydroformylating α-olefins present in a mixture of α-olefins and internal olefins, said hydroformylation being catalyzed by a class of ligand-stabilized platinum (II) dihalide complexes in combination with Group IVB metal halides.

5 Claims, No Drawings

SELECTIVE HYDROFORMYLATION PROCESS

This application is a continuation-in-part of Ser. No. 251,639 filed in the United States Patent Office on May 8, 1972.

SUMMARY OF THE INVENTION

This invention relates to the selective and preferential addition of hydrogen and carbon monoxide to alpha olefins contained in mixtures of alpha and internal olefins to obtain carbonyl containing compounds using improved ligand-stabilized, platinum(II) dihalide complexes with Group IVB metal halides.

More specifically, this invention concerns the preferential hydroformylation of alpha olefins contained in alpha-olefin-internal olefin mixtures by the addition of hydrogen and carbon monoxide, under relatively mild reaction conditions using the above described three component, homogeneous, ligand-stabilized platinum-(II) catalysts.

BACKGROUND OF THE INVENTION

Aldehydes, particularly linear paraffinic aldehydes, are extremely useful as intermediates in organic synthesis because of their terminal carbonyl group which is among the most active groupings in organic compounds. For instance, they are easily reduced and oxidized and take part in a number of addition reactions. More specifically, paraffinic (alkyl) aldehydes are readily catalytically reduced to the primary alcohols, and oxidized to the corresponding carboxylic acids. They also undergo addition and/or condensation reactions with hydrogen cyanide, alcohols, nitroparaffins as well as condensations with themselves and other carbonyl-containing compounds. Further, these aldehydes condense with ammonia and its derivatives including primary amines. The latter condensation products (which are commonly known as Schiff bases) lend themselves to applications as surfactants or detergents when solubilized by processes such as sulfation or oxyalkylation.

In the aforementioned pending application the applicants disclosed novel three component, ligand stabilized, homogeneous hydroformylation catalysts consisting essentially of (1) platinum(II) dihalides, stabilized with (2) one or more Group VB, VIB or VIIB donor ligands and used in combination with (3) Group IVB metal halide co-catalysts.

It has now been demonstrated that under relatively mild reaction parameters some of these homogeneous catalysts have the unexpected ability to preferentially and selectively hydroformylate alpha-olefins contained in alpha-olefin-internal olefin mixtures to the substantial exclusion of hydroformylating the internal olefins in the mixture. That is, as long as the mixture of olefins contains a substantial quantity of alpha (or 1-) olefins in addition to internal (non-terminal) olefins, preferential hydroformylation of the alpha olefin takes place until 80–95% conversion of the alpha-olefin fraction is converted to the linear aldehyde containing 1 more carbon atom than the original 1-olefin.

This finding of selective and preferential hydroformylation is both surprising and unexpected since the hydroformylation of both alpha olefins alone and internal (non-terminal) olefins alone has been demonstrated in the aforementioned pending parent application using the novel three component platinum(II) hydroformylation catalysts of this invention.

In the broadest contemplated practice of this invention, selective and preferential hydroformylation of alpha-olefins in alpha-olefin-internal olefin mixtures containing a significant quantity of internal olefin takes place by: contacting the olefin mixture with at least a catalytic quantity of a three (3) component, ligand-stabilized, homogeneous platinum(II) catalyst complex consisting of (1) a platinum(II) dihalide, stabilized with (2) at least one Group VB donor ligand in combination with (3) a Group IVB metal halide co-catalyst, at elevated temperatures and superatmospheric conditions of pressure, with a gaseous mixture of hydrogen and carbon monoxide until about 80–95% of the alpha-olefins are selectively converted to linear aldehydes, and optionally separating the linear aldehydes contained therein.

In a preferred and more specific embodiment of the above-described process, essentially linear alkyl aldehyde products containing from 3 to 31 carbon atoms are prepared by the catalytic addition of hydrogen and carbon monoxide to an alpha-olefin-internal olefin mixture containing from about 10 to 90 mole % of internal olefins, said olefins containing 2 to 30 carbon atoms, by the process of:

a. admixing each mole of olefin contained in said mixture to be hydroformylated in a deoxygenated reaction media, with from 0.001 to 0.1 moles of a three component ligand-stabilized, homogeneous platinum-(II) catalyst complex consisting essentially of (1) platinum(II) dihalide stabilized with (2) at least one Group VB donor ligand selected from the group consisting of trivalent phosphorus and trivalent arsenic bonded to one or more hydrocarbyl radicals, said radicals being selected from the group consisting of aryl, alkyl and substituted aryl radicals containing less than 20 carbon atoms, and (3) a tin(II) halide, said mole ratio of tin(II) halide to said ligand-stabilized platinum(II) dihalide complex ranging from 1/1 to 10/1, in the presence of sufficient inert solvent to disperse the components of the admixture, to form a deoxygenated reaction mixture.

b. pressurizing said reaction mixture to between about 100 psig to 3000 psig with at least sufficient carbon monoxide and hydrogen to satisfy the stoichiometry of the hydroformylation reaction referred to supra, said mole ratio of $H_2:CO$ ranging from 30:1 to 1:30 moles of hydrogen for each mole of carbon monoxide;

c. heating said pressurized reaction mixture to temperatures between 25° to 125° C, until about 80 to about 95% of the alpha olefins contained in said olefin mixture is converted, then d. isolating said linear aldehyde products contained therein.

In order to further aid in the understanding of this invention, the following additional disclosure is submitted.

A. PROCESS SEQUENCE AND VARIATIONS

In general, the components of the hydroformylation reaction mixture, including optional inert solvent, alpha-olefin-internal olefin mixture and catalyst may be added in any sequence as long as good agitation is employed to provide a good dispersion or a homogeneous reaction mixture. For example, the following represent some variations insofar as the addition of catalyst components, inert solvents and olefin addition that may be made without departing from the inventive process. These modifications include:

1. The catalyst may be preformed and added preformed to the reaction solvent prior to the addition of the olefin mixture and other inert solvent components.

2. Preferably, to minimize stability problems with the catalyst, the catalyst is best formed in situ usually by mixing the deoxygenated inert solvent and neat olefin mixture, followed by the addition of the excess metal halide of Group IVB, and finally by the addition of the ligand-stabilized platinum(II) complex to form the reaction mixture.

3. After using either variation 1 or 2, the deoxygenated catalyst containing reaction mixture is pressurized with CO and hydrogen and heated until the aldehyde product is formed.

4. An especially preferred embodiment, which minimizes both the induction period and the isomerization of the olefin mixture is the following: the catalyst is formed in a deoxygenated solvent; the catalyst solution is pressurized with carbon monoxide and hydrogen and heated to the desired reaction temperature; the olefin mixture is then added neat or dissolved in a suitable solvent. The reaction mixture is agitated under CO and $H_2$ at the desired reaction temperature until the aldehyde product is formed.

B. THREE COMPONENT LIGAND-STABILIZED HOMOGENEOUS PLATINUM(II)-GROUP IVB METAL HALIDE CATALYST COMPOSITION

The ligand-stabilized, platinum(II) halide, Group IVB metal halide complexes are known in the literature and methods for their preparation have been described*. One convenient mode of preparation in situ is to mix a solution of platinum(II) halide complex such as $PtCl_2[P(C_6H_5)_3]_2$, with a large molar excess of Group IVB metal halide, preferentially $SnCl_2$.

* For example: R. D. Cramer et al, J. A. Chem. Soc., 85 1691(1963)

The three component ligand stabilized, homogeneous platinum(II) catalyst composition consists essentially of:
 1. platinum(II) halides
 2. Group VB donor ligands, and
 3. Group IVB metal halides 1. The platinum(II) halide component employed in the catalyst composition are preferably the dichloride or the dibromide, in that order. These dihalides, in order to be effective for the selective and preferential hydroformylation process, must include at least one Group VB donor ligand and Group IVB metal halides, described more fully below:

2. Each Group VB donor ligand contains one or more phosphorus or arsenic atom, preferably in the trivalent state, bonded to one or more hydrocarbyl radicals, said radicals being selected from the group consisting of aryl, alkyl, and substituted aryl radicals containing less than 20 carbon atoms;

3. Group IVB metal halides which can be utilized with the first two components [platinum(II) halides and Group VB donor ligands] include tin(II) chloride, tin(II) bromide, tin(II) iodide, tin(IV) chloride, and germanium(II) chloride.

Illustrative of suitable Group VB ligands which may be used with platinum(II) halides to form selective hydroformylation catalysts in the presence of suitable Group IVB metal halides are:

$PtCl_2[As(C_6H_5)_3]_2$-$SnCl_2$,
$PtCl_2[P(C_6H_5)_3]_2$-$SnCl_2$,
$PtCl_2[P(C_2H_5)_2(C_6H_5)]$-$SnCl_2$,
$PtCl_2[As(n\text{-}C_4H_9)_3]_2$-$SnCl_2$,
$PtCl_2[(C_6H_5)_2P(CH_2)_2P(C_6H_5)_2]$-$SnCl_2$,
$PtCl_2[(C_6H_5)_2AsCH_2CH_2As(C_6H_5)_2]$-$SnCl_2$,
$PtCl_2[P(n\text{-}C_4H_9)_3]_2$-$SnCl_2$,
$PtCl_2[P(CH_3)_2C_6H_5]_2$-$SnCl_2$,
$PtCl_2[P(p\text{-}CH_3OC_6H_4)_3]_2$-$SnCl_2$,
$PtCl_2[P(OC_6H_5)_3]_2$-$SnCl_2$,
$PtCl_2]P(p\text{-}CH_3 \cdot C_6H_4)_3]_2$-$SnCl_2$, as well as the corresponding tin(II) bromide, tin(II) iodide, tin(IV) chloride, and germanium(II) halide complexes. Tables I and II show evidence of the suitability of the above class of ligand-stabilized platinum-(II)-Group IV metal halides complexes as selective and preferentially hydroformylation catalysts.

C. TEMPERATURE REQUIRED FOR HYDROFORMYLATION

The temperature range which can be employed for hydroformylation is a variable which is dependent upon experimental factors including the olefin employed, the total pressure, the mole ratio of hydrogen and carbon monoxide used, the concentrations of reactants and catalyst and particularly the choice of platinum catalyst among other things. Using an alpha olefin-internal olefin mixture containing a typical linear alpha olefin and $PtCl_2P(C_6H_5)_3$-$SnCl_2$ as a representative catalyst, an operable temperature range is from about 25° to 125° C at superatmospheric pressures of greater than 100 psig.

D. PRESSURES REQUIRED FOR HYDROFORMYLATION

The pressure range which can be employed for hydroformylation is a variable which is also dependent on the factors mentioned above. Using $PtCl_2[P(C_6H_5)_3]_2$-$SnCl_2$ as a representative catalyst, and 1-heptene as the linear alpha olefin component, an operable pressure range is from 100 to 3000 psig, with a mole ratio of $H_2$:CO being 1:1, when a temperature range of from about 25° to 125° C is employed.

E. HYDROGEN TO CARBON MONOXIDE RATIO

The $H_2$/CO mole ratio may be varied over a range of from 30/1 to 1/30 when suitable temperatures and total pressures are employed. A preferred narrower range is from 2/1 to 1/2 of hydrogen/carbon monoxide.

F. REACTION TIMES REQUIRED

As previously indicated in the analogous discussion above, experimental variables are important in arriving at reaction times. Generally, substantial conversions (about 80 to 95%) of the alpha-olefin in the alpha-olefin-internal olefin mixture to the linear paraffinic aldehydes can almost always be accomplished within 20 hours, with 4 to 6 hours representing the more usual reaction time interval.

G. RATIO OF TIN(II) HALIDE TO LIGAND-STABILIZED PLATINUM(II) COMPLEX

While the molar ratio of tin(II) chloride to the ligand-stabilized platinum(II) halide complex is not critical, the experimental work performed indicates that at least 1 mole of tin(II) chloride for each mole of ligand-stabilized platinum(II) chloride complex is required for reproducibility and good selectivity. Preferably a ratio of from about 2 to 8 moles of tin(II) chloride for each mole of ligand-stabilized platinum(II) complex has been established to give the optimum amount of linear paraffinic aldehyde at greatly increased rates of hydroformylation. This preferred ratio is based upon the hydroformylation of 1-heptene.

H. RATIO OF LIGAND-STABILIZED PLATINUM(II) HALIDE-CATALYST COMPLEX TO TOTAL OLEFIN SUBSTRATE

Experimental work indicates that a molar ratio of up to about 500 moles of 1000 moles of total olefin (alpha olefin plus internal olefin) per mole of platinum metal complex can be employed in most instances. This minimal ratio of about 0.001 moles of catalyst per mole of total olefin is herein referred to as a "catalytic ratio" or "catalytic amount." Much lower ratios (i.e. 25 moles of olefin substrate per mole of platinum catalyst complex) are not harmful but are economically unattractive. For this reason the favored mole ratio range arrived at in Table II ranges from 100 to 500 moles of total olefin per mole of platinum catalyst complex.

I. INERT SOLVENTS

The preferential or sequential hydroformylation is run most conveniently in the presence of an inert diluent. Experimental data indicate the preferred solvents are polar ketones such as acetone, methyl ethyl ketone, diethyl ketone, methyl propyl ketone, methyl isobutyl ketone, and acetophenone. However, other solvents inert to hydroformylation can be used. These include aromatics such as benzene, toluene, xylenes and the like. Preferably the reaction is run in the presence of sufficient inert solvent to disperse the components of the reaction mixture. Excess inert solvent does not appear to be harmful.

J. ALPHA OLEFINS IN THE OLEFIN MIXTURE AS SUBSTRATES

Alpha olefins or 1-alkenes in the alpha olefin-internal olefin mixture can range in carbon content from 2 up to 30 carbon atoms and containing 1 double bond can be employed as the alpha olefin substrates in the olefin mixture for the preferential or sequential hydroformylation reaction. A favored range of alpha-olefins are those containing 3 to 14 carbon atoms. Illustrative alpha ($\alpha$) or terminal olefin (or 1-alkene) substrates include 1-propene, 1-butene, 1-pentene, 1-hexene, 1-heptene, 1-octene, 1-nonene, 1-decene and 1-tetradecene. Internal olefin substrates in the mixture may also contain from 2 to 30 carbon atoms. The carbon range spread between the alpha olefins in the mixture does not appear to be critical to success. For example, preferential hydroformylation between 1-alkenes and internal alkenes has been observed when the alpha-olefin-internal olefin have the same number of carbon atoms.

Illustrative internal olefins which can be present in the alpha olefin-internal olefin mixture include linear internal olefins such as 2-hexene, 2-pentene, 2-octene, 5-decene, 4-octene, etc., cyclic olefins including cyclohexene, 1-methyl-1-cycloheptene, cyclooctene, etc., and branched internal olefins such as 3-ethyl-2-pentene, 2,3-dimethyl-2-butene, etc. These olefin substrates may be utilized in conjunction with one or more inert background solvents such as those mentioned above. The olefins can range in carbon content from 2 to 30 carbon atoms and can be in the form of single, discrete compounds or in the form of mixtures of olefins with or without large quantities of saturated hydrocarbon. Insofar as is known the ratio of alpha-olefin to internal olefins is not critical as long as at least 10 mole% of the olefin mixture is alpha-olefin. Table II shows data for the hydroformylation of various, alpha-olefin-internal olefin mixtures which lend themselves to sequential hydroformylation.

K. BY-PRODUCTS

As far as can be determined, without limiting the invention thereby, olefin hydroformylation catalyzed by the homogeneous platinum(II) catalyst complexes of this invention leads to the formation of only three minor classes of by-products. These are isomerized olefins, hydrogenated olefins and high boiling products, assumed to be condensation type products, which do not readily elute from the gas chromatography column used to follow the course of hydroformylation.

The by-products may be separated from the linear paraffinic aldehydes by the usual chemical or physical techniques, such as distillation, solvent extraction, chromatography etc.

L. IDENTIFICATION PROCEDURES are by one or more of the following analytical procedures — gas chromatography (g.c.) infrared, elemental analysis and nuclear magnetic resonance. Unless otherwise specified all percentages are by mole ratio rather than weight or volume, and all temperatures are in centigrade rather than fahrenheit.

M. CONVERSION as defined herein represents the extent of transformation of the reaction olefin to other products. Conversion is expressed as a percentile and is calculated by dividing the amount of olefin consumed during hydroformylation by the amount of olefin originally charged and multiplying the quotient by 100.

N. YIELD as defined herein, represents the efficiency in catalyzing the desired hydroformylation reaction relative to other undesired reactions. In this instance hydroformylation of 1-alkenes to linear paraffinic aldehyde is the desired conversion. Yield is expressed as a percentile, and is calculated by determining the amount of linear paraffinic aldehyde product formed, divided by the amount of linear aldehyde which theoretically can be formed and multiplying the quotient obtained by 100.

O. SELECTIVITY as defined herein is the efficiency in catalyzing a desired hydroformylation reaction relative to other undesired reactions. When $\alpha$-olefins are to be hydroformylated, hydroformylation to the linear paraffinic aldehyde is the desired conversion. Selectivity is expressed as a percentile, and is calculated by determining the amount of linear aldehyde product formed, divided by the total amount of aldehyde products formed and multiplying the quotient obtained by 100.

Having described the inventive process in general terms, the following examples are submitted to supply specific and illustrative embodiments.

EXAMPLE 1

Preferential Hydroformylation of Propene in Propene-2-Hexene Mixtures Using $PtCl_2[P(C_6H_5)_3]_2$-$SnCl_2$ As Catalyst To an appropriately sized glass liner of a mechanically stirred autoclave charged with 100 ml of deoxygenated methyl isobutyl ketone (MIBK) is added under nitrogen purge 0.56g of $SnCl_2$-$2H_2O$(2.5 mmole) and 0.40g of $PtCl_2[P(C_6H_5)_3]_2$ (0.5 mmole) previously formed. The catalyst components are stirred for 5 minutes producing a yellow-green catalyst solution with some undissolved catalyst remaining. The autoclave is then sealed, deoxygenated, and the sealed catalyst solution heated to 65° C under 50 psig of an equi-volume, hydrogen-carbon monoxide gas mixture. A mixture of 2.1g of propene (50 mmole) and 12.4 ml of 2-hexenes (mixed cis and trans isomers, 100 mmole) is injected into the reactor, and the total pressure is raised to 1260 psig with an equi-volume of $H_2$/CO. Liquid samples are removed periodically and the clear yellow-green solutions are analyzed immediately by gas chromatography. After 6 hours the heating is terminated, the reactor is cooled, vented and 92 ml of a clear light yellow solution free of solids is recovered. Analysis provided the following data:

a. For the Propene Fraction

Propene conversion (mole, %) — > 90
Major product — n-butyraldehyde
n-butyraldehyde selectivity — 91%
n-butyraldehyde yield (mole, %) — 85
Rate of n-butyraldehyde formation — 0.08 M/hr.

b. For the 2-Hexene Fraction

2-Hexene conversion (mole, %) — 2
Major Product — iso-heptaldehydes

The above run shows yield and selectivity to n-butyraldehyde are comparable to those obtained during the hydroformylation of the alpha-olefin alone.

EXAMPLES 2 to 7

Preferential Hydroformylation of Propene in Propene-2-Hexene Mixtures Using Other Platinum Homogeneous Catalysts Using the same olefinic substrate mixture, the same solvents, reaction parameters and apparatus the work of Example 1 is repeated with the platinum homogeneous catalysts listed in Table I. In all instances when the monitoring of the reactions indicated more than 85% conversion, the reactions are terminated and analysis shows n-butyraldehyde selectivity of between 80 to 95% and yields of n-butyraldehyde between 80 to 90%. 2-hexene conversions are less than 5–8 mole % and the major product is isoheptaldehyde.

TABLE I

| EXAMPLE | LIGAND-STABILIZED PLATINUM(II)-GROUP IVB METAL HALIDE COMPLEX |
| --- | --- |
| 2 | $PtCl_2[P(p-CH_3 \cdot C_6H_4)_3]_2$—$SnCl_2$ |
| 3 | $PtCl_2[P(n-C_4H_9)_3]_2$—$SnCl_2$ |
| 4 | $PtCl_2[As(C_6H_5)_3]_2$—$SnCl_4$ |
| 5 | $PtCl_2[P(C_6H_5)_3]_2$—$GeCl_2$ |
| 6 | $PtCl_2[P(CH_3)_2C_6H_5]_2$—$SnCl_2$ |
| 7 | $PtCl_2[P(OC_6H_5)_3]_2$—$SnCl_2$ |

EXAMPLE 8

Selective Hydroformylation of 1heptene in a 1-Heptene-2-Octene Mixture

This experiment is quite similar to that of Example 1, in that the apparatus, operating procedure, solvent, temperature and $H_2$/CO pressures are unchanged, however in this run the olefin charge is an equimolar mixture of 1-heptene and 2-octene (50 mmole of each olefin). The results are as follows:

a. For the 1-Heptene Fraction

1-Heptene Conversion (Mole, %) — > 95
Major Product — n-octylaldehyde
n-octylaldehyde Selectivity — 97%
n-octylaldehyde yield (mole, %) — 82
Rate of n-octylaldehyde formation — 0.07 M/hr.

b. For the 2-Octene Fraction

2octene conversion (mole, %) — 1.0
Major Product — iso-nonaldehydes
Iso-nonaldehyde yield (mole, %) — 1.0

EXAMPLE 9

Sequential Hydroformylation of Propene-2-Hexene Mixtures

Once again the procedure, apparatus, olefins, platinum catalyst and reaction parameters disclosed in Example 1 are followed. The only differences of substance are the mole ratio of propene to 2-hexene, which is 1:2 in Example 1, is charged to 2:1, and, more importantly, hydroformylation is carried out 10 hours beyond the 6 hour period used in Example 1 in order to determine if the 2-hexene fraction present after propene hydroformylation is complete could also be hydroformylated to iso-heptaldehydes using the same reaction conditions and catalyst. The results are presented below:

a. For the Propene Fraction (after 6 hours)

Propene Conversion (Mole, %) > 95
Major product — n-butyraldehyde
n-butyraldehyde selectivity — 91%
n-butyraldehyde yield (mole %) — 91
Rate of n-butyraldehyde formation — 0.1 M/hr.

b. For the 2-Hexene Fraction (After 16 hours)

2-Hexene Conversion (mole, %) — 10–20
Major Product — iso-heptaldehydes
iso-heptaldehyde yield (mole %) — 16

The above data confirm that after the initial selective or preferential hydroformylation of the 1-alkene (propene) fraction to n-butyraldehyde is essentially complete (>95% conversion after about 6 hours), the remaining 2-hexene fraction may be hydroformylated to iso-heptaldehydes using the same catalyst solution and the same reaction conditions. In this way, the complex $PtCl_2[P(C_6H_5)_3]_2$-$SnCl_2$ allows sequential hydroformylation of the α-olefin-internal olefin mixture of propene and 2-hexene.

EXAMPLES 10 TO 15

Selective Hydroformylation of Other Mixtures of 1-Olefins-Internal Olefins

In these examples, summarized in Table II, the procedure is similar to preceding examples, particularly regarding the operating temperatures (65°–80° C), pressures, ratios of $H_2$ to CO, and catalyst compositions and concentrations (2.5–5mM Pt). The major differences of substance are in the identity of the components of the olefin mixture and in the initial molar ratio of total olefin charge (alpha olefin plus internal olefin) per mole of platinum(II) catalyst complex. Example 11 uses benzene as the inert solvent, Example 12 uses mixtures of 1-olefin and internal olefin having the same carbon number.

As the runs in Table II show, the initial reaction is selective hydroformylation of the alpha (α) olefin fraction. After 6 hours hydroformylation, an average conversion of the 1-olefin component of about 80% is obtained. Again, as in the preceding example 9, substantial sequential hydroformylation of the internal olefin fraction begins to take place after the hydroformylation of the 1-alkene has been completed (See Example 15). Furthermore, the selective hydroformylation of 1-alkene to the linear aldehyde takes place even when a mixture of several 1-alkenes and internal olefins are present in the mixture (Example 14).

For instance, numerous stabilizing ligands containing Group VB donor atoms, particularly trivalent phosphorus and arsenic atoms bonded to various organic aryl, substituted aryl and alkyl radicals, such as triphenylarsine, and triphenylphosphine in combination with platinum(II) halide salts and Group IVB metal halides such as tin(II) chloride combine to give highly active and

TABLE II

| Ex. | Olefin Mixture | [Olefin]/[Pt] Ratio | Catalyst | Reaction Time (Min) | Olefin Conv. (Mole %) | Major Aldehydic Products Identity | Selectivity (%) | Yield (Mole %) |
|---|---|---|---|---|---|---|---|---|
| 10 | 1-Tetradecene | 50 | $PtCl_2[P(p-CH_3 \cdot C_6H_4)_3]_2$—$SnCl_2$ | 360 | 80 | n-Pentadecylaldehyde | 97 | 78 |
|  | 5-Decene | 50 |  |  | <1 | None | — | — |
| 11[a] | 1-Nonene | 50 | $PtCl_2[As(C_6H_5)_3]_2$—$SnCl_2$ | 360 | 5 | n-Decylaldehyde | 95 | <2 |
|  | 2-Methyl-2-Butene | 450 |  |  | <1 | None | — | — |
| 12 | 1-Octene | 450 | $PtCl_2[P(CH_3)_2C_6H_5]_2$—$SnCl_2$ | 360 | 95 | n-Nonaldehyde | 95 | 93 |
|  | 1-Methyl-1-Cycloheptene | 50 |  |  | <1 | None | — | — |
| 13 | 1-Heptene | 50 | $PtCl_2[P(p-CH_3O \cdot C_6H_4)_3]_2$—$SnCl_2$ | 360 | 85 | n-Octylaldehyde | 97 | 78 |
|  | 2-Hexene | 50 |  |  | <1 | None | — | — |
| 14 | 1-Heptene | 50 | $PtCl_2[P(C_6H_5)_3]_2$—$SnCl_2$ | 360 | 88 | n-Octylaldehyde | 95 | 81 |
|  | 1-Decene | 50 |  |  | 77 | n-Undecylaldehyde | 95 | 67 |
|  | 2-Hexene | 50 |  |  | <2 | iso-Heptaldehydes | — | <2 |
|  | 2-Octene | 50 |  |  | <2 | iso-Nonaldehydes | — | <2 |
| 15 | 1-Octene | 50 | $PtCl_2[P(C_6H_5)_3]_2$—$SnCl_2$ | 2,400 | 98 | n-Nonylaldehyde | 94 | 81 |
|  | 2-Hexene | 50 |  |  | 20 | iso-Heptaldehydes | N.D.[b] | 18 |

[a]Solvent is benzene
[b]N.D.=Not determined

EXAMPLE 16

Hydroformylation of 1-Heptene-N-Hexane Mixtures

This experiment demonstrates that a typical 1-heptene can be hydroformylated even in very dilute concentrations in a typical n-alkane solvent mixture.

The charge is a mixture of 3.5 ml of 1-heptene (25 mmole) which is diluted with 14.5 ml of n-hexane to about 20% (volume to volume) concentration. Reaction conditions, platinum catalyst solution and other variables are the same as described in Example 1. The results follow:

1-Heptene conversion (mole,%) — 100
Major product — n-octaldehyde
n-octaldehyde (selectivity) — 96%
n-octaldehyde yield (mole, %) — 74%
Rate of n-octaldehyde formation — 0.07 M/hr.
n-hexane loss — < 0.3%

As the numerous examples of this invention indicate, the subject invention is advantageous in several respects compared to corresponding hydroformylation of the prior art. For example, using various ligand-stabilized platinum(II) halide, Group IVB metal halide (3 component) catalyst complexes, 1-alkenes contained in mixtures with internal alkenes and cycloalkenes, can be selectively and preferentially hydroformylated to linear aldehydes at relatively mild reaction conditions of temperature and pressure even when there is little or no spread in carbon content between 1-alkenes and internal alkenes in the mixture. Further selectivities to the 1-aldehydes are generally excellent, and competing isomerization and reduction reactions are kept to a minimum by terminating the reaction when 80 to 95% of the 1-alkenes are converted. In addition, large ratios of alkene to catalyst may be employed and generally most oxygenated and aromatic solvents are suitable as reaction media.

Finally, the invention is quite advantageous in that numerous substitutions, modifications and changes can be made without departing from the inventive concept.

selective hydroformylation catalysts. However, the scope of the subject invention can best be understood by examining the claims which follow, in conjunction with the preceding specification.

What is claimed is:

1. A process for preparing primarily linear aldehyde products by the selective and catalytic hydroformylation of alpha-olefins contained in a mixture of alpha-olefins and internal olefins, wherein said alpha-olefins in the mixture constitute from 10 to 90 mole % of the olefin mixture, said alpha and internal olefins containing from 2 to 30 carbon atoms, by:

A. contacting each mole of said alpha-olefins and internal olefins in said mixture to be hydroformylated in a deoxygenated environment, with from about 0.001 to 0.1 moles of a three component, ligand stabilized, homogeneous platinum(II) catalyst complex selected from the group consisting of:

$PtCl_2[P(C_6H_5)_3]_2$-$SnCl_2$,
$PtCl_2[P(p-CH_3 \cdot C_6H_4)_3]_2$-$SnCl_2$,
$PtCl_2[P(n-C_4H_9)_3]_2$-$SnCl_2$,
$PtCl_2[As(C_6H_5)_3]_2$-$SnCl_4$
$PtCl_2[P(C_6H_5)_3]_2$-$GeCl_2$,
$PtCl_2[P(CH_3)_2C_6H_5]_2$-$SnCl_2$,
$PtCl_2[P(p-CH_3O \cdot C_6H_4)_3]_2$-$SnCl_2$,
$PtCl_2[P(OC_6H_5)_3]_2$-$SnCl_2$ and
$PtCl_2[As(C_6H_5)_3]_2$-$SnCl_2$, said tin(II) or germanium(II) chlorides mole ratio to said ligand stabilized platinum(II) catalyst complex ranging from about 2:1 to 8:1, in the presence of sufficient inert solvent to disperse the components of the admixture, to form a deoxygenated reaction mixture, B. pressurizing said reaction mixture to between about 100 psig to 3,000 psig with a sufficient equivolume admixture of a gaseous hydrogen to carbon monoxide, to satisfy the stoichiometry of the aldehyde-forming hydroformylation reaction, C. heating said pressurized reaction admixture between 25° to 125° C until between about 80% to about 95% of said alpha-olefins contained in said olefin mixture is converted to linear aldehyde, and then D. isolating said linear aldehyde products contained therein.

2. The process of claim 1 wherein said homogeneous ligand stabilized catalyst is prepared in situ by adding as separate components of the reaction mixture a ligand-stabilized platinum(II) dihalide complex and a molar excess of Group IVB metal halide.

3. The process of claim 1 wherein said alpha-olefin fraction present in the alpha-olefin-internal olefin mixture consists of a mixture of different alpha-olefins.

4. The process of claim 3 wherein said alpha-olefins are selected from the group consisting of propene, 1-heptene, 1-nonene and 1-tetradecene.

5. The process of claim 1 wherein said internal olefin fraction present in the alpha-olefin-internal olefin mixture is selected from the group consisting of linear internal olefins, cyclic olefins and branched internal olefins.

* * * * *